United States Patent
Labyed et al.

(10) Patent No.: US 10,512,452 B2
(45) Date of Patent: Dec. 24, 2019

(54) TISSUE CHARACTERIZATION IN MEDICAL DIAGNOSTIC ULTRASOUND

(71) Applicant: Siemens Medical Solutions USA, Inc., Malvern, PA (US)

(72) Inventors: Yassin Labyed, Maple Valley, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 614 days.

(21) Appl. No.: 15/209,180

(22) Filed: Jul. 13, 2016

(65) Prior Publication Data

US 2018/0014814 A1    Jan. 18, 2018

(51) Int. Cl.
*A61B 8/08* (2006.01)
*A61B 8/00* (2006.01)

(52) U.S. Cl.
CPC ............ *A61B 8/5223* (2013.01); *A61B 8/485* (2013.01); *A61B 8/08* (2013.01); *A61B 8/461* (2013.01); *A61B 8/5207* (2013.01)

(58) Field of Classification Search
CPC ......... A61B 8/5223; A61B 8/485; A61B 8/08; A61B 8/461; A61B 8/5207
USPC ....................................................... 600/438
See application file for complete search history.

(56) References Cited

U.S. PATENT DOCUMENTS

| | | | |
|---|---|---|---|
| 9,244,169 B2 | 1/2016 | Fan et al. | |
| 2007/0161902 A1* | 7/2007 | Dan | A61B 8/481 600/458 |
| 2013/0345565 A1* | 12/2013 | Fan | A61B 8/08 600/442 |
| 2014/0018679 A1* | 1/2014 | Chen | A61B 8/085 600/438 |
| 2014/0206995 A1* | 7/2014 | Oikawa | A61B 8/4227 600/438 |

OTHER PUBLICATIONS

Lin Xin Yao et al, Backscatter coefficient measurements using a reference phantom to extract depth-dependent instrumentation factors, Ultrasonic Imaging vol. 12, Issue 1, Jan. 1990, pp. 58-70 (Year: 1990).*
Ki Lee et al, Frequency dependencies of phase velocity and attenuation coefficient in a water-saturated sandy sediment from 0.3 to 1.0 MHz, J Acoust Soc Ann. May 2007;121(5 Pt1):2553-8. (Year: 2007).*
Labyed et al., Estimate of the attenuation coefficient using a clinical array transducer for the detection of cervical ripening in human pregnancy, Ultrasonics. Jan. 2011 ; 51(1): 34-39. doi:10.1016/j.ultras.2010.05.005 (Year: 2011).*

* cited by examiner

*Primary Examiner* — Pascal M Bui Pho
*Assistant Examiner* — John Denny Li

(57) ABSTRACT

For estimating attenuation in ultrasound imaging, displacements at different locations along an acoustic radiation force impulse (ARFI) beam are used measured. The on-axis displacements and displacements from a phantom using a same ARFI focus as a reference are used to cancel out focusing effects. A single ARFI beam may be used to estimate the attenuation for a location.

17 Claims, 5 Drawing Sheets

TISSUE CHARACTERIZATION IN MEDICAL DIAGNOSTIC ULTRASOUND

BACKGROUND

The present embodiments relate to medical diagnostic ultrasound. In particular, ultrasound is used to characterize tissue.

Important pathological information may be obtained by characterizing the ultrasound attenuation of tissue. The level of attenuation may be a biomarker for fatty liver disease. Cancers, such as breast cancer, may be diagnosed, in part, based on attenuation of ultrasound.

Attenuation may be measured using spectral analysis of radio frequency backscatter signals. A change in amplitude of power spectra as a function of depth of the acoustic backscatter indicates the attenuation. These backscatter approaches may suffer from variability, even with spectral averaging.

U.S. Pat. No. 9,244,169 teaches a technique to measure attenuation using acoustic radiation force impulses (ARFIs). ARFIs at different frequencies are transmitted, and attenuation is estimated from displacements responsive to the ARFIs. Use of multiple ARFIs may result in inaccuracies due to motion. Focusing effects may also contribute to inaccuracy.

BRIEF SUMMARY

By way of introduction, the preferred embodiments described below include a method, system, computer readable medium, and instructions for characterizing tissue in ultrasound imaging. Displacements at different locations along an ARFI beam are used to estimate attenuation. The on-axis displacements and displacements from a phantom using a same ARFI focus as a reference are used to cancel out focusing effects. A single ARFI beam may be used to estimate the attenuation for a location.

In a first aspect, a method is provided for characterizing tissue with a medical diagnostic ultrasound scanner. A transducer of the ultrasound scanner transmits an acoustic radiation force impulse as a transmit beam along a scan line in a patient. The ultrasound scanner measures displacements as a function of time along the scan line. At least some of the displacements are responsive to the acoustic radiation force impulse. An image processor determines a characteristic of the displacements as a function of time for each of a plurality of locations along the scan line, calculates a log of a ratio of the characteristic to a characteristic of a phantom for each of the locations, fits a line to the log of the ratio as a function of the locations, and calculates an attenuation coefficient, absorption coefficient, scattering coefficient, elastic modulus, or combinations thereof using the line. An image of the attenuation coefficient, absorption coefficient, scattering coefficient, elastic modulus, or combinations thereof is generated on a display.

In a second aspect, a system is provided for ultrasound imaging. A transmit beamformer is configured to transmit an acoustic pushing pulse to a focal region in a patient. A receive beamformer is configured to output samples for regions on-axis with the pushing pulse. An image processor is configured to determine displacements for the regions from the samples and to calculate an attenuation of tissue in the patient from the displacements. A display is configured to display the attenuation.

In a third aspect, a method is provided for ultrasound imaging with a medical diagnostic ultrasound scanner. A beamformer of the ultrasound scanner tracks displacements along an axis of excitation of an acoustic radiation force impulse in a tissue of a patient. The displacements are caused by the acoustic radiation force impulse. An image processor of the ultrasound scanner estimates an attenuation from the displacements along the axis. The attenuation is transmitted.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Ultrasound attenuation is estimated using ARFI and a reference phantom. ARFI-induced displacements are measured at locations along the axis of excitation. Displacements tracked along the axis of excitation of ARFI push pulses in a tissue of interest and in a well-characterized tissue mimicking phantom are measured using the same transmit-receive conditions. The on-axis displacements from both are used to estimate the ultrasound attenuation coefficient (absorption+scattering), absorption attenuation coefficient, scattering attenuation coefficient, and/or elastic modulus. Unlike conventional ultrasound backscatter methods for estimating attenuation, the proposed method has a higher resolution and smaller variance in the estimates.

A single ARFI may be used. In other embodiments, ARFIs at different frequencies are transmitted to estimate a frequency-dependent ultrasound attenuation.

Figure 1:
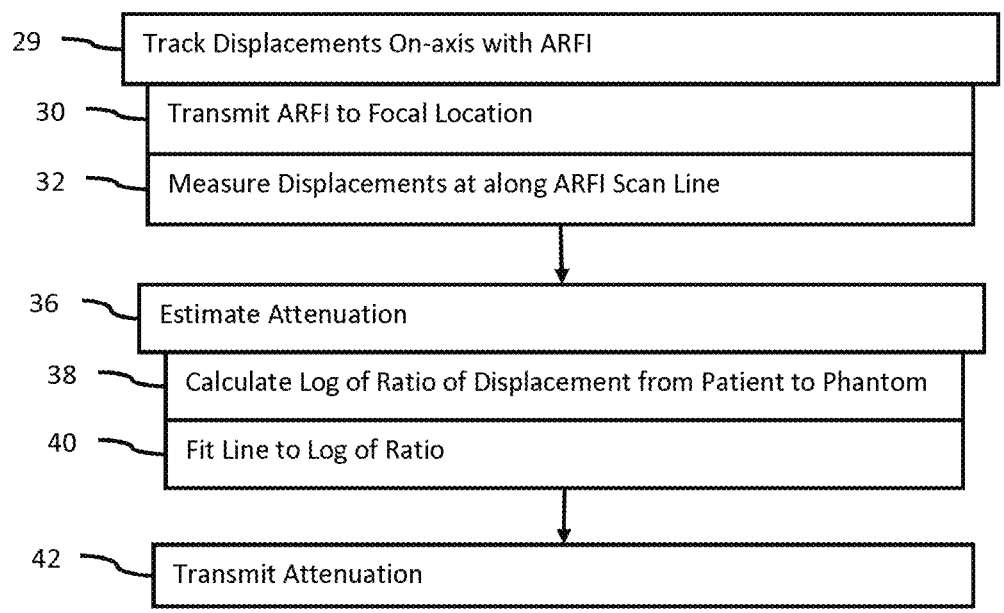
FIG. 1 is a flow chart of one embodiment of a method for estimating attenuation with a medical diagnostic ultrasound scanner.

FIG. 1 shows one embodiment of a flow chart diagram of a method for ultrasound imaging with a medical diagnostic ultrasound scanner. The method characterizes tissue using displacements measured in response to and at locations on-axis with an ARFI. By using a log of a ratio of displacements from tissue of a patient to displacements from a phantom with a known attenuation, the focusing effects may be reduced. Attenuation of the tissue of the patient may be estimated from a slope of a line fit to the log of the ratio over depth.

Figure 8:
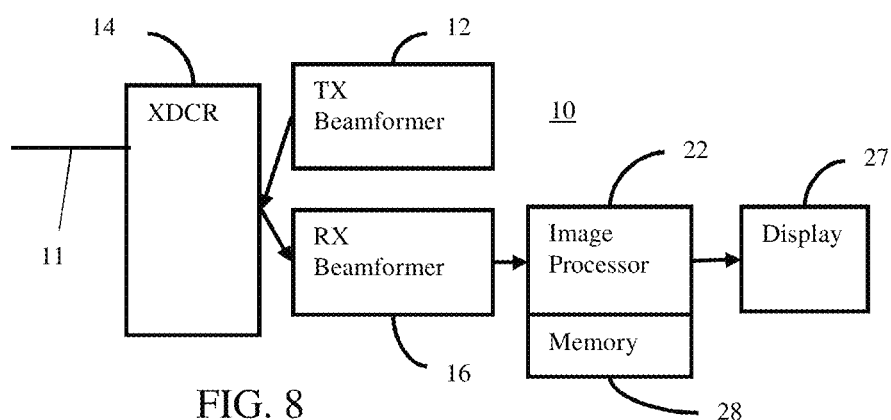
FIG. 8 is a block diagram of one embodiment of a system for ultrasound imaging.

The method is performed by the ultrasound imaging system 10 of FIG. 8, the image processor 22, or a different system and/or processor. For example, the ultrasound imaging system 10 acquires samples for measuring displacement with the transmit and receive beamformers 12, 16 and the transducer 14, and the image processor 22 estimates the attenuation from the samples. The display 27 displays the estimated tissue characteristic (e.g., attenuation).

The acts of FIG. 1 are performed in the order shown (top to bottom) or a different order. For example, the samples for displacement are measured in act 32 prior to and after performing act 30.

Additional, different, or fewer acts than shown in FIG. 1 may be used. For example, act 42 is not performed. As another example, acts for scanning and generating B-mode or other ultrasound images are added.

In act 29, the ultrasound scanner tracks displacements on-axis with ARFI. The beamformer tracks, in part. The beamformer is used to generate the ARFI and to sample the tissue response for calculating displacements. The displacements caused by a pushing pulse (i.e., ARFI) are tracked along the scan line of the pushing pulse. The tracking is performed for tissue of a patient. The tissue response of a patient is tracked during examination of the patient.

Using the same transmit and receive focusing and configuration, tracking is also performed in a phantom. The tracking in the phantom is performed at any time, such as prior to or after manufacture or as part of calibration. The same or similar type of ultrasound scanner with the same or similar transducer is used to measure displacements in the phantom. The measurements or information derived from the measured displacements (e.g., peak displacement amplitude) are loaded into and/or stored in the ultrasound scanner for estimating attenuation in the patient. The known attenuation for the phantom is also loaded into and/or stored in the ultrasound scanner. Through transmissions or other measurements may be used to determine the attenuation of the phantom with any desired accuracy. Other tissue characteristics than attenuation may be obtained for the phantom, such as elastic modulus, scattering coefficient, and/or absorption coefficient. The information from the phantom is used as a reference, so the calibration or other acquisition of the phantom information may be done once or periodically by the manufacturer or other person.

Acts 30 and 32 are used to perform the tracking of act 29. Other tracking may be used.

In act 30, the ultrasound scanner uses the transducer to apply stress to the tissue. For example, ARFI focused at a region of interest or a point is transmitted. When the ARFI is applied to a focused area, a shear and/or longitudinal wave may be induced and propagate away from this focused area. These generated waves are not measured. The ARFI stresses the tissue. The tissue responds to the stress by moving, which is the movement that is measured. Relative to an original location or relaxed state, tissue is displaced. At the focal region or other locations within the transmit beam, this displacement increases and then recovers to zero, resulting in a temporal displacement profile. The tissue properties affect the displacement over time at various depths caused by the ARFI.

The impulse may be generated by a cyclical pulsed waveform of any number of cycles (e.g., tens or hundreds of cycles). For example, acoustic radiation force is transmitted as an impulse for applying stress to tissue. The impulse wavefront propagates to the region of interest, causing movement of the tissue.

Figure 2:
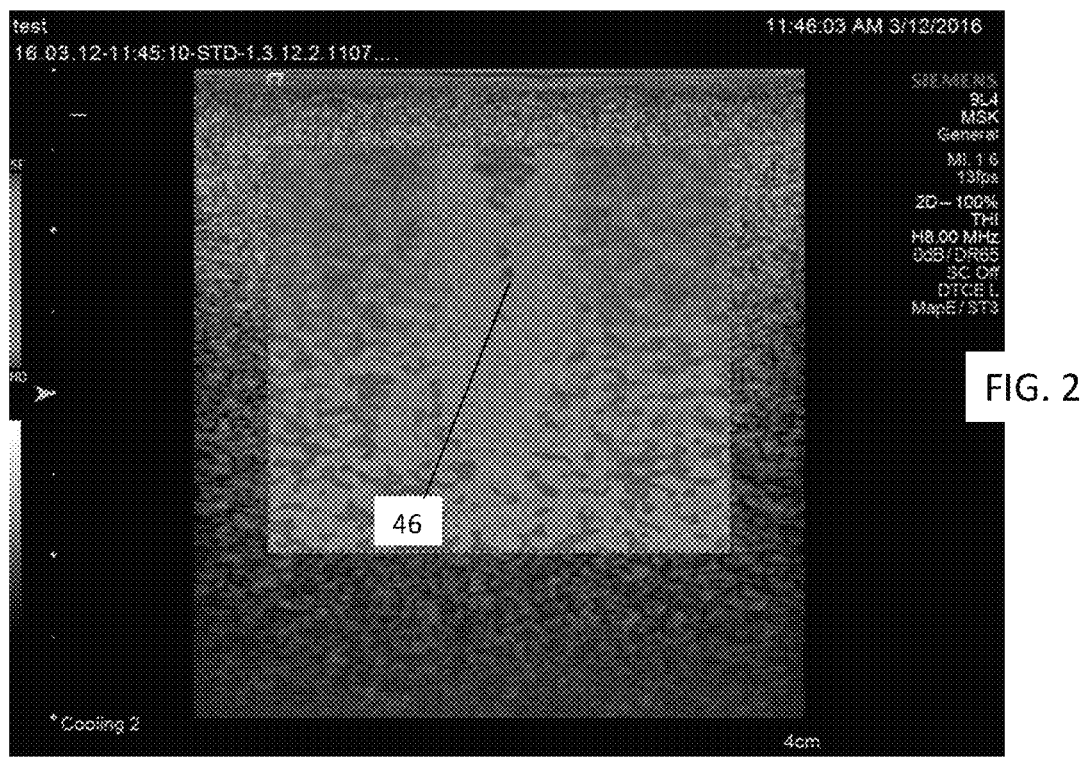
FIGS. 2 and 3 are example displacement images showing beam profiles of ARFI transmit beams in phantoms with different attenuation.
Figure 3:
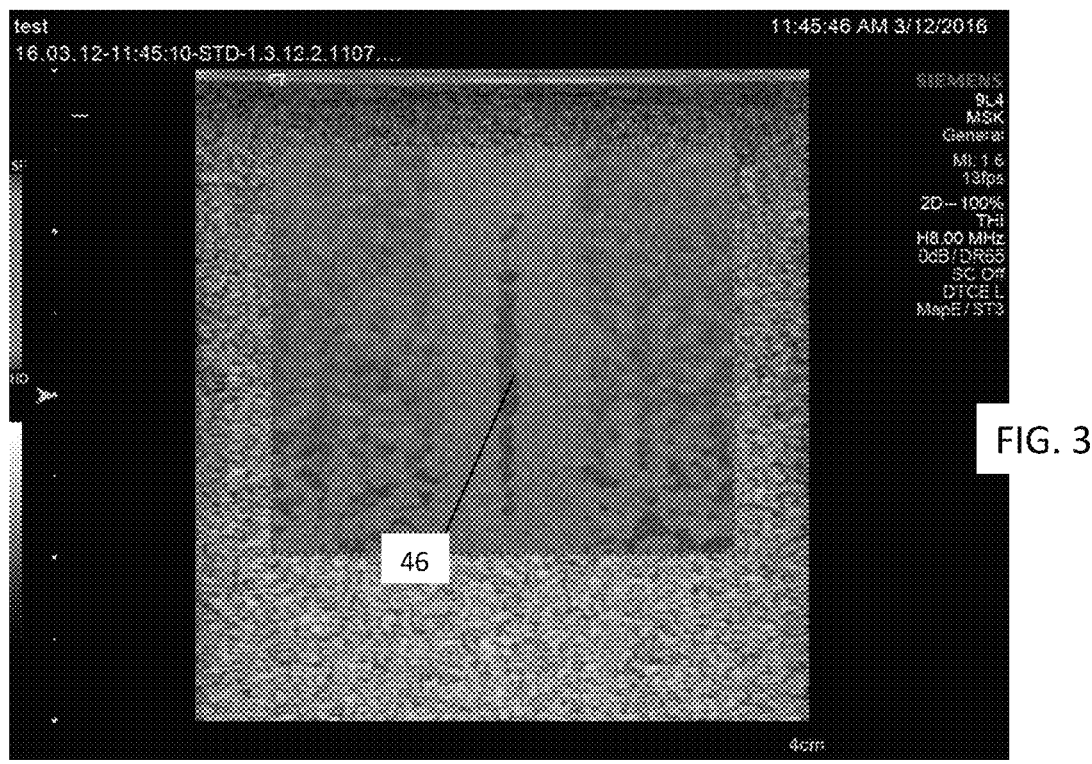

FIGS. 2 and 3 show example beam profiles for ARFI transmit beams with the same focusing and beamforming but in phantoms with different attenuation characteristics. The beam profiles are shown by measuring displacement of tissue. FIG. 2 is a displacement map of an ARFI push pulse focused at 2 cm in a phantom of attenuation 4.16 dB/cm at 4 MHz. FIG. 3 is a displacement map of an ARFI push pulse focused at 2 cm in a phantom of attenuation 2 dB/cm at 4 MHz. To measure displacements in an area shown in FIGS. 2 and 3, multiple push pulses and tracking are used within the ROI.

In each of FIGS. 2 and 3, the ARFI transmit beam is transmitted along a scan line. The transmit beam has a profile relative to this scan line. The beam profile appears as a vertical column in the examples of FIGS. 2 and 3. A center of the column includes a region 46 of greater intensity. This region 46 includes the focal location of the transmit beam. The transmit beam has a beam profile marked by locations of greater acoustic intensity along a scan line. The acoustic intensity decreases with further lateral and/or depth spacing from the focal region. The region 46 or beam profile may be defined based on an amount of reduction from a peak intensity, such as 3 dB, 6 dB, 10 dB, 20 dB or other amount of roll-off. Within the beam profile, greater acoustic intensity is provided.

Act 32 occurs while the tissue is being subjected to and/or recovers from the stress. For example, transmission and reception occurs after application or change in the stress and before the tissue reaches a relaxed state. For reference to determine magnitude of displacement, transmission and reception occurs prior to ARFI application and/or after the tissue relaxes to a steady state.

In act 32, the ultrasound scanner measures displacements over time. The ultrasound scanner uses a transmit beamformer to transmit a sequence of transmit beams. For a transmit event, a transmit beam is formed. The pulses to form the transmit beams are of any number of cycles. For example, 1-3 cycles are used. Any envelope, type of pulse (e.g., unipolar, bipolar, or sinusoidal), or waveform may be used.

A plurality of ultrasound signals is transmitted to the tissue responding to the stress. The plurality of signals is transmitted in separate transmit events. A transmit event is a contiguous interval where transmissions occur without reception of echoes responsive to the transmission. During the phase of transmitting, there is no receiving. Where a sequence of transmit events is performed, a corresponding sequence of receive events is also performed in act 32. A receive beamformer of the ultrasound scanner generates samples in response to each transmit event. A receive event is performed in response to each transmit event and before the next transmit event.

The transducer receives ultrasound echoes in response to each transmit event. The transducer converts the echoes to receive signals, which are receive beamformed into ultrasound data representing a plurality of spatial locations. The ultrasound scanner receives a sequence of receive signals where receive beams are received in response to each of the transmit beams in the transmit sequence.

The reception is interleaved with the transmission of the sequence. For each transmit event, a receive event occurs. The receive event is a continuous interval for receiving echoes from the depth or depths of interest. The event occurs after ceasing the transmit event. After the transducer completes generation of acoustic energy for a given transmission, the transducer is used for reception of the responsive echoes. The transducer is then used to repeat another transmit and receive event pair for the same spatial location or locations, providing the interleaving (e.g., transmit, receive, transmit, receive, . . . ) to measure the tissue response over time.

The measurement of displacements of the tissue is along an axis of excitation by the ARFI in the tissue of the patient. For example, the measurements are performed for the region 46, such as a range of locations around a focal location of the ARFI transmission. Rather than tracking outside the region 46 for laterally moving shear wave-caused displacements, the displacement directly caused by the ARFI at the focal location and/or other locations in the region 46 of maximum or greater acoustic intensity is measured. The measurements occur for locations along the ARFI axis or scan line. The samples for measuring displacements are acquired over time as the tissue displaces and within the beam profile along the scan line.

The response of tissue is detected at different depths along one or more receive scan lines within the region 46. Doppler or B-mode scanning may be used for measuring motion of the tissue responding to the stress. Ultrasound imaging is performed before, during and/or after the ARFI stress is applied. Ultrasound data is received in response to transmissions of ultrasound. The transmissions and receptions are performed along a line, over an area, or over a volume. A sequence of transmissions and receptions are provided for each spatial location to track over time.

In one embodiment, the receive beams for measuring displacement are along the same scan line as the ARFI transmit beam. The transmit and receive beams for tracking are collinear with each other and the ARFI transmit beam. In other embodiments, parallel receive beamformation is used. Two or more (e.g., 4) receive beams are formed in response to each transmit beam. The receive beams are within the region 46 but may be spaced from the transmit scan line, providing samples for a region about a location. Similarly, the depths for the samples used are within the region 46 at multiple depths. The samples are positioned at locations having an acoustic intensity in the ARFI transmit beam that is at least 3 dB of location of a peak acoustic intensity in the ARFI transmit beam (e.g., focal depth location). For example, the locations are in the region 46. Locations outside the 3 dB intensity may be used.

The beamformed data or samples are acquired as the tissue undergoes displacement. Some samples of the tissue in the relaxed state may be acquired. For example, the samples are acquired prior to application of the ARFI and after application of the ARFI. Prior to application, the tissue may be in a relaxed state or free of ARFI induced displacement. Once the ARFI transmission occurs, the tissue is moved so that subsequent samples are of the tissue in the displaced state until the tissue returns to a relaxed state. The sampling occurs over any range of times, such as starting before or after the ARFI transmit beam and continuing for any amount of time after ARFI ceases. The samples are acquired at a plurality of times.

The samples are radio frequency (RF) or in-phase and quadrature (IQ) data output by a receive beamformer. In response to a transmission of acoustic energy (e.g., a transmit beam), acoustic echoes impinge upon elements of a transducer. The elements convert the acoustic echoes into electrical signals. The receive beamformer coherently sums the signals from different elements to determine the response of tissue at particular sample locations. The output of the receive beamformer is RF or IQ data.

The displacements are measured from the samples. The ultrasound scanner determines tissue motion. Tissue motion is detected as a displacement in one, two, or three dimensions. Motion responsive to the ARFI transmit beam may be detected. The tissue motion is detected at different times. The different times correspond to the different tracking scans (i.e., transmit and receive event pairs).

A reference sample or samples are acquired with the tissue in the relaxed data and are used to determine displacement at other times. Tissue motion is detected by estimating displacement relative to the reference tissue information. For example, the displacement of tissue along one or more receive scan lines is determined. The displacement may be measured from tissue data, such as B-mode ultrasound data, but flow (e.g., velocity) or IQ information prior to detection may be used.

Correlation, cross-correlation, minimum sum of absolute differences or other similarity measure is used to determine the displacement between scans (e.g., between the reference and the current). Data representing spatial locations distributed about a location of measurement is correlated with the reference data. For each depth or spatial location, correlations over a plurality of depths or spatial locations is performed. The spatial offset with the highest or sufficient correlation at a given time indicates the amount of displacement for that location. For each location, the displacement as a function of time is determined.

Two or three-dimensional displacement in space may be used. One-dimensional displacement along a direction different from the scan lines or beams may be used.

The displacement measurements are performed for any number of scan lines. For example, four receive beams are formed in response to each transmission. For each depth, the displacements from different receive beams may be combined, such as averaged. In other embodiments, only a single receive beam or other numbers of receive beams are formed in response to each transmission.

After transmitting the acoustic force to displace the tissue, B-mode transmissions and receptions are performed repetitively along any number of scan lines within the region 46. Some of the ultrasound data, such as at the beginning or end of the repetitions, may not be responsive to the tissue displacement, so is similar to the reference. Each repetition monitors a same region or locations for determining tissue response for those locations. By repeating the transmitting of the ultrasound pulses and the receiving of the ultrasound echoes over the time, the displacements over the time are determined. Any number of M repetitions may be used, such as repeating about 50-100 times. The repetitions occur as frequently as possible while the tissue recovers from the stress, but without interfering with reception. The tissue temporal displacement profile is obtained by repeatedly transmitting to and receiving signals from the same target area in a similar way as the Doppler method does.

Figure 4:
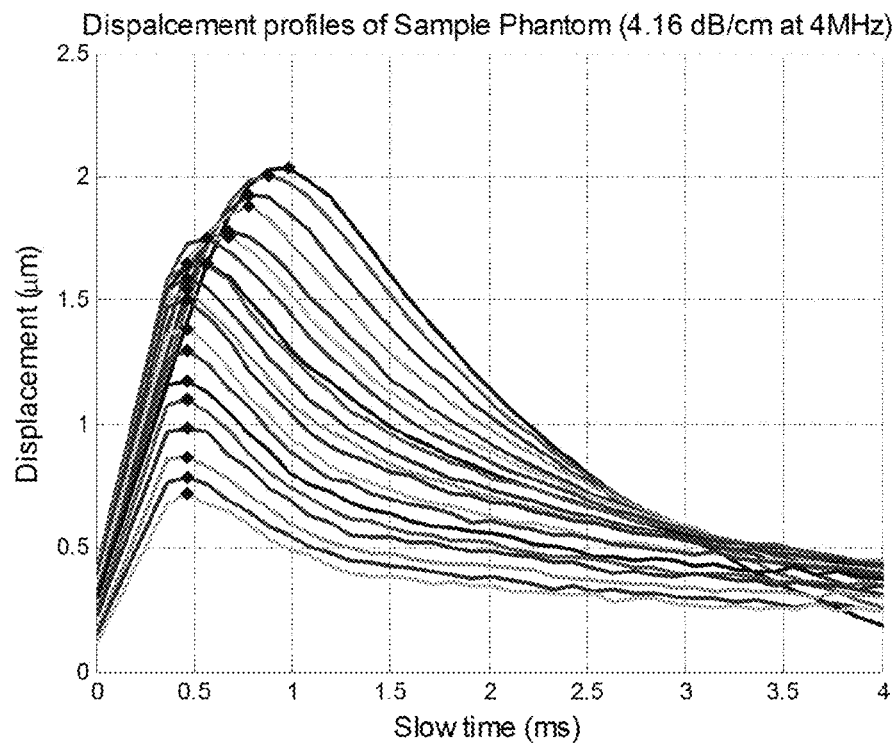
FIGS. 4 and 5 show example time-domain displacement profiles of the phantoms.
Figure 5:
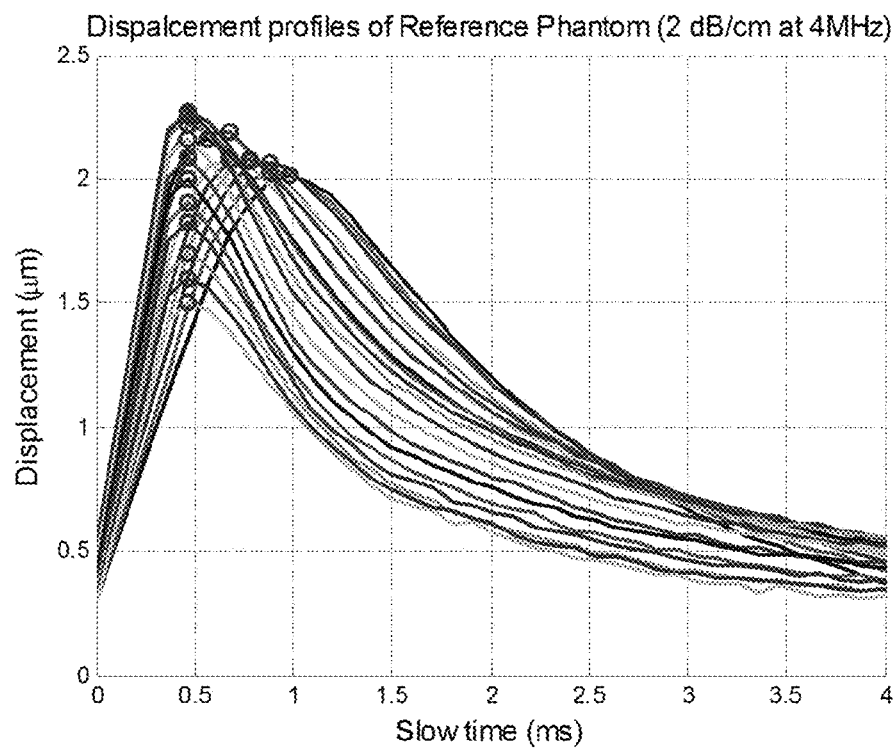

FIGS. 4 and 5 show example on-axis displacement profiles for different locations along the ARFI axis in the phantoms used in FIGS. 2 and 3, respectively. The magnitude of the displacement over time is shown. In the examples of FIGS. 4 and 5, multiple laterally spaced displacements are measured for each depth and averaged. The displacement profiles shown in FIGS. 4 and 5 are created from the lateral averages. The displacements for a given depth may be responsive to a same ARFI or different ARFIs transmitted in sequence with focus at different locations.

While two phantoms are used in FIGS. 2-5, one phantom is treated as measurements from a patient and the other as phantom-based reference measurements. For example, FIGS. 2 and 4 are used to represent patient tissue measurement (sample) while FIGS. 3 and 5 are used to represent phantom measurements (reference). The displacement is measured from a phantom for FIGS. 2 and 4, but would be measured from sampled tissue of a patient in actual use.

Time 0 is the time of the ARFI transmit beam. Times 0.1-4.0 are displacements measured at different beamformer sample locations along the ARFI scan line after ARFI transmission. The tissue in the region 46 generally displaces due to the ARFI rather than a shear or longitudinal wave generated by the ARFI transmit beam. This displacement is around 0 prior to the ARFI transmit beam, then increases to about 2.0-2.3 um at an ARFI focal location within a fraction of a millisecond, then moves back towards and passes the relaxed state. After 0.5 to 1.0 milliseconds, the displacement progresses towards the relaxed state. Different displacement profiles occur for different depths. Due to differences in attenuation, the displacement profiles in FIG. 4 are different than the displacement profiles in FIG. 5 despite using a same ARFI focus, amplitude, apodization, aperture, and other beamformer settings.

In act 36 of FIG. 1, an image processor of the ultrasound scanner estimates the attenuation for the tissue of the patient. The attenuation for the sampled region is estimated from the displacements in the region. The displacements along the axis of the ARFI are used to estimate the attenuation. As reflected in FIGS. 4 and 5, the attenuation causes a variation in amplitude of the displacement as a function of location along the scan line.

Acts 38 and 40 show one example approach to estimate attenuation. In other approaches, the change in amplitude over location or depth is used without the log, ratio, and/or line fitting.

The displacements of tissue of the patient along the axis and displacements along the axis from the reference phantom are used in combination to estimate the attenuation and reduce the influence of ARFI focusing and/or amplitude. The tissue displacement, S, at axial position $z+z_0$ from an ARFI push pulse is give by:

$$S(z+z_0) = \frac{cI(z+z_0)e^{-2\alpha z}\alpha_a}{E}$$

where c is a constant accounting for the attenuation along the propagation path to $z_0$, $I(z+z_0)$ is the acoustic intensity at axial position $z+z_0$, $\alpha_\alpha$ is the absorption coefficient, E is the elasticity of the tissue, and a is the ultrasound attenuation coefficient (np/cm). $\alpha$ is the local attenuation coefficient in a ROI ($z_0$ to $z_0+\Delta z$) along the ARFI scan line and not the attenuation along the propagation path. The attenuation coefficient $\alpha$ includes both absorption and scattering attenuation.

To normalize the effects of focusing, the displacements from a reference phantom of known attenuation coefficient using the same ARFI settings are used. The ratio of the displacements in the tissue sample (e.g., FIGS. 2 and 4) to the displacements in the reference (e.g., FIGS. 3 and 5) from an ARFI pulse is given by:

$$R(z) = e^{-2(\alpha-\alpha')z}\frac{\alpha_a E'}{\alpha_{a'} E}$$

where $\alpha'$, E', and $\alpha_{\alpha'}$ are the attenuation coefficient, the elasticity modulus, and the absorption coefficient of the reference phantom. These reference values are known or measured previously. The ratio removes the effects of ARFI focusing or amplitude (c/(z) is cancelled out).

The ratio uses a characteristic of the displacements or displacement profiles. In one embodiment, the image processor determines the characteristic of the displacements as a function of time as a maximum displacement over time. For each of a plurality of locations along the scan line, the maximum displacement is found. Other characteristics may be used. For example, the displacement profiles are transformed into a frequency domain (Fourier transformation) and a characteristic of the frequency response of the displacement profiles for each location is determined.

Figure 6:
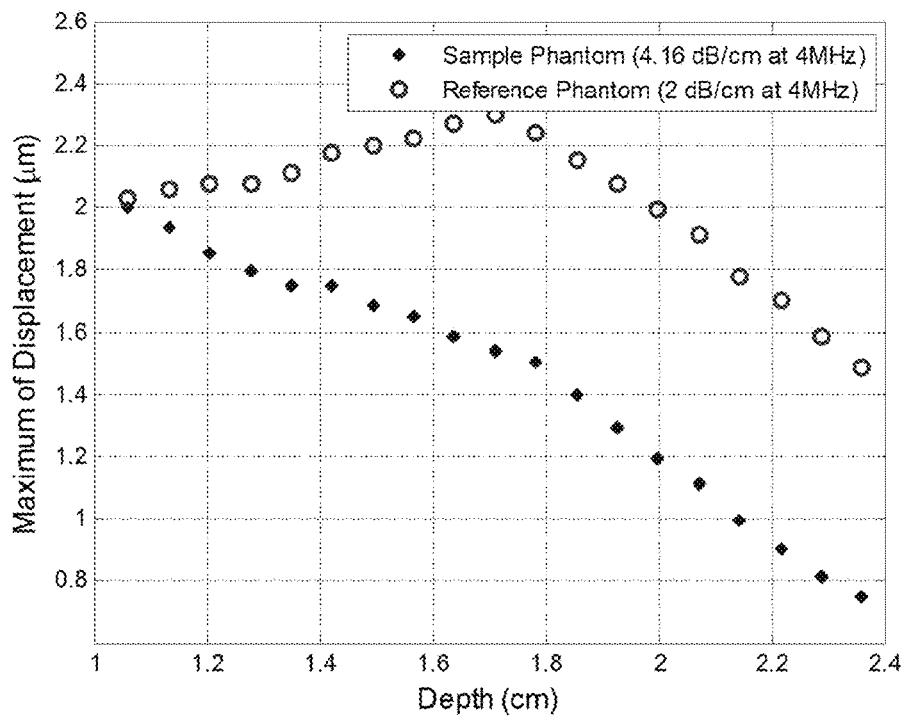
FIG. 6 shows example peak displacements as a function of location along the ARFI axis.

The same determination is made for the sampling from the patient and the sampling from the phantom. The determination for the phantom may be pre-determined, such as loading the values for maximum displacement into the scanner without loading or having the reference displacements. The values of the characteristic for the locations for the reference as well as the currently examined patient are obtained. The maxima or peak amplitude of each displacement profile is marked in FIGS. 4 and 5. The maxima are shown as dots in FIG. 4 and circles in FIG. 5. FIG. 6 shows a plot or graph of the maxima for the patient and the phantom as a function of depth over a depth range of 1.0-2.4 cm. In this example, the ARFI push pulse is focused at 2 cm. Other depth ranges including or not including a focal depth may be used. The maxima are along the scan line or axis for the ARFI transmission. The displacement profiles of FIG. 4 are used to represent patient measurements, and the displacement profiles of FIG. 5 are used to represent the reference measurements.

In act 38 of FIG. 1, the image processor calculates a log of a ratio of the characteristic from the patient to the phantom. For example, the ratio of the maximum displacement of the tissue in the patient to the maximum displacement of the phantom is calculated for each location or depth. The ratio provides relative information between the patient and the phantom with the known attenuation. Other relative measures than ratio may be used, such as a sum, product, average, difference, or more complex value of relationship.

For each of the locations or depths, the log of the ratio of the maximum displacement to a phantom maximum displacement is calculated. The log converts the relationship into a linear domain. Computing the log of the ratio is represented as:

$$\ln(R(z)) = -2(\alpha-\alpha')z + \ln\left(\frac{\alpha_a E'}{\alpha_{a'} E}\right)$$

Figure 7:
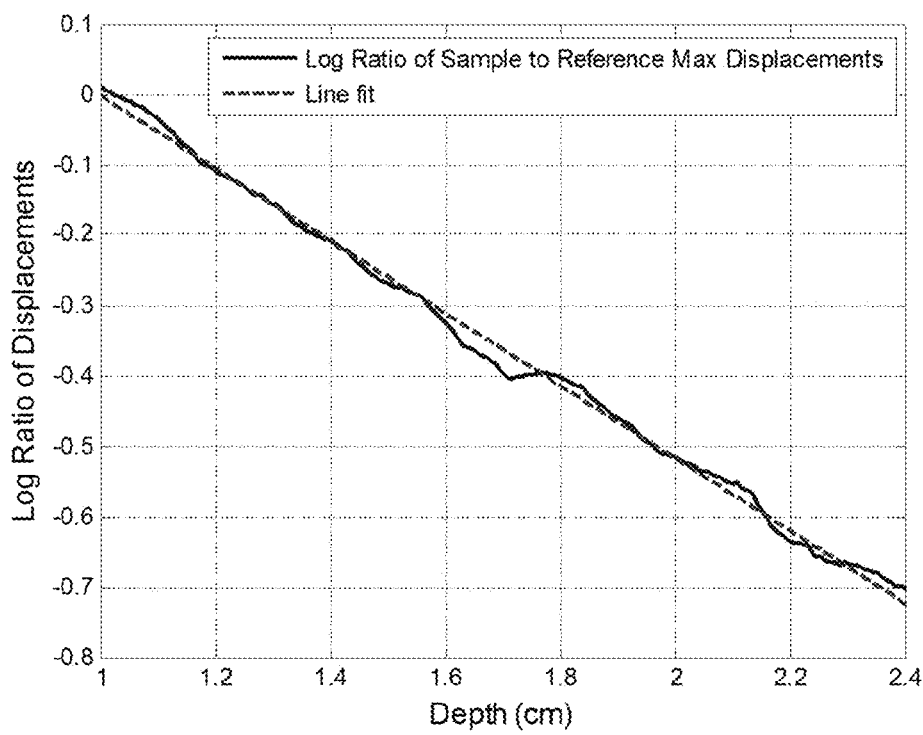
FIG. 7 shows an example line fit to a log of a ratio of peak displacements from the different phantoms.

The log ratio of the maximum displacements from the sample to that of the reference is calculated. FIG. 7 shows a plot of the log of the ratio of the maximum displacements from FIG. 6. Other conversions may be used.

In act 40, the image processor fits a line to the log of the ratio or other relative measure. The line is fit as a function of the locations or depth. Any line fitting may be used, such as a least squares fit. FIG. 7 shows a dashed line as fit to the plot of the log of the ratio. The line is fit to the relationship between the patient measurements and the reference or phantom measurements.

In an alternative embodiment, an exponential fit without performing the natural log is used. For example, the exponential fit is represented as:

$$ae^{bz} \text{ where } a = \frac{\alpha_a E'}{\alpha_{a'} E} \text{ and}$$

$$b = -2(\alpha-\alpha') \text{ fit to } R(z)e^{-2(\alpha-\alpha')z\frac{\alpha_a E'}{\alpha_{a'} E}}.$$

Other fits may be used.

In act 36 of FIG. 1, the image processor calculates the attenuation coefficient, absorption coefficient, scattering coefficient, elastic modulus, or combinations thereof using the line or characteristic of a fit exponential. The line is used below. The fit line has a slope and intercept. The slope, intercept, or other characteristic of the fit line is calculated and used to estimate the tissue characteristic.

The attenuation is calculated from the slope of the line. The slope represents an attenuation coefficient as the slope reflects the relative decay in amplitude of the displacement characteristic. The log of the ratio is linear with respect to z, so the slope of the line that fits the log-ratio with respect to z is:

$$\text{slope} = -2(\alpha - \alpha'),$$

resulting in the attenuation being:

$$\alpha = -\frac{\text{slope}}{2} + \alpha'.$$

The known attenuation of the phantom and the slope provide for the attenuation in the tissue of the patient. In the example of FIG. 7, the attenuation coefficient is estimated as 4.19 dB/cm at 4 MHz (center frequency of the ARFI transmission) for the phantom being used to represent tissue of a patient (i.e., displacements of FIGS. 2 and 4). Since a phantom is used instead of measuring an actual patient, the attenuation of 4.19 dB/cm as estimated using on-axis displacements may be compared to the known attenuation for that phantom: 4.12 dB/cm. Greater or lesser accuracy may be provided for actual patient measures.

The image processor calculates the elastic modulus, the absorption coefficient, or both from an intercept of the fit line. The elasticity or elastic modulus E or the absorption coefficient $\alpha_a$ may be estimated from the intercept of the line if one or the other is known, as represented by:

$$E = e^{-\text{interecpt}} \frac{E' \alpha_a}{\alpha_{a'}}$$

$$\alpha_a = e^{\text{interecpt}} \frac{E \alpha_{a'}}{E'}$$

The elasticity or absorption coefficient may be assumed or assigned a predetermined value based on the tissue being scanned in order to calculate the other. Alternatively, the elasticity is measured from shear wave or other ultrasound imaging. With the elasticity for a location or region being measured, the acoustic absorption is calculated from the intercept, known absorption coefficient of the phantom or reference and known elasticity of the phantom or reference. In yet another approach, an iterative or optimization solution is used to match possible estimates of the elasticity and the acoustic absorption to the measured intercept and attenuation.

The image processor calculates the scattering coefficient using the slope and the intercept. The scattering attenuation coefficient is given by: $\alpha_s = \alpha - \alpha_a$. Since the attenuation is a function of the slope and the acoustic absorption is a function of the intercept, the scattering is calculated from both using the attenuation and acoustic absorption.

Any of the characteristics may be calculated for a single region or multiple regions. Different spatial windows may be used to calculate attenuation by region. The process with the ARFI focused at different locations and/or using different frequencies may be used to determine the attenuation by location and/or frequency.

In act 42, the image processor, a display, a communications interface, or other device transmits the attenuation and/or other tissue characteristic calculated from the log of the ratios. The transmission is from and/or within the ultrasound scanner. The transmission is to another device, such as a memory, display, network, server, workstation, patient record database, and/or picture archiving and communications server. The attenuation, elasticity modulus, absorption coefficient, and/or scattering coefficient are transmitted as data or imbedded in an image.

In one embodiment, the transmission is to a display. A value that is a function of the attenuation or other tissue characteristic is displayed. The value is displayed as alphanumeric text. The value is the characteristic itself (e.g., value for attenuation) and/or is derived from the characteristic. In alternative or additional embodiments, the value is included as part of a graph, such as displaying the attenuation as a function of frequency or location.

In another embodiment, the value is part of an image spatially representing the tissue characteristic. For example, the attenuation is measured at two or more different locations. For depth, different windows or depth ranges may be used to calculate attenuation in response to one ARFI. For laterally spaced locations, acts 29-40 are repeated. In response to one ARFI transmission, the tissue displacements at different locations in the transmit beam profile of the ARFI transmission are measured and used to estimate location specific tissue characteristic. Acts 29-40 are repeated for different regions 46 laterally. The ARFI transmit is repeated for different tissue locations. The values of the tissue characteristic for the different locations modulate the color, brightness, and/or shade of the image. Different pixels in the image show the corresponding tissue characteristic values through this modulation.

An image may include values for various of the tissue characteristics. For example, text, graphs, or pixel modulation are used for two or more of the attenuation coefficient, absorption coefficient, scattering coefficient, or elastic modulus.

The value is displayed alone or with another image. For example, a B-mode image or other image is provided with the value or values representing the tissue characteristic. Where the tissue characteristic is measured for multiple locations, a color or other modulation in a region of interest in the B-mode image is displayed. Where the tissue characteristic is measured for one or more locations, alphanumeric text showing the value or values is provided as an annotation or overlay on the B-mode image.

In one embodiment, shear wave imaging is performed. The shear wave speed is indicated at a user or processor selected location. Using the same ARFI used to generate the shear wave or a different ARFI, the attenuation or other tissue characteristic is calculated for that same location and presented. The scans used to calculate displacements for shear wave speed may also be used to calculate displacements on-axis, such as using parallel receive beamforming. Without additional sequencing or transmissions and receptions, both the shear wave speed and attenuation or other tissue characteristic are provided to the user for diagnosis. The values are provided in a same image, adjacently displayed images, or sequentially displayed images.

FIG. 8 shows one embodiment of a medical system 10 for ultrasound imaging. The medical system 10 measures the attenuation and/or other tissue characteristics. For example, the medical system 10 implements the method of FIG. 1 or another method. The medical system 10 is an ultrasound scanner using measures of tissue displacement on axis with and due to ARFI rather than shear or longitudinal wave induced by the ARFI. By using measurements for a same ARFI configuration but in a phantom with known attenuation, the patient measured displacements are used to determine acoustic attenuation for diagnostic use by a physician.

The medical system 10 includes a transmit beamformer 12, a transducer 14, a receive beamformer 16, an image processor 22, a memory 28, and a display 27. Additional, different or fewer components may be provided. For example, the medical system 10 includes a B-mode or other detector. As another example, the image processor 22, memory 28, and/or display 27 are provided without the front-end components, such as the transmit and receive beamformers 12, 16. In yet another example, a user interface including a user input (e.g., mouse, trackball, keyboard, buttons, knobs, sliders, and/or touch pad) is provided for user indication of a region of interest on an image.

In one embodiment, the medical system 10 is a medical diagnostic ultrasound system. In an alternative embodiment, the system 10 is a computer or workstation.

The transducer 14 is an array of a plurality of elements. The elements are piezoelectric or capacitive membrane elements. The array is configured as a one-dimensional array, a two-dimensional array, a 1.5 D array, a 1.25 D array, a 1.75 D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams into a patient. Vector®, sector, linear or other scan formats may be used.

The transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion, and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, and/or combinations thereof. A transmit beam origin, orientation, and focus are generated based on these beamforming parameters.

The transmit beamformer 12 generates a transmit beam for ARFI and transmit beams for measuring resulting displacements. The transmit beam for ARFI is formed at different energy or amplitude levels than the transmit beams for measuring displacements. Amplifiers for each channel and/or aperture size control the amplitude of the transmitted beam. Transmit beams to displace tissue may have greater amplitudes than for imaging or measuring tissue displacement. Alternatively or additionally, the number of cycles in the pulse or waveform used to generate ARFI is greater than for tracking (e.g., 100 or more cycles for ARFI and 1-6 cycles for tracking).

The ARFI transmit beam is transmitted as an acoustic pushing pulse. The transmit beam is focused at a location, causing increased acoustic intensity at the location and surrounding locations along a scan line. Similarly, transmit beams for measuring the tissue displacement at the focal location or locations of increased intensity of the ARFI transmission are generated along the same scan line and/or to the same locations.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays and/or phase rotations, are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. In alternative embodiments, the receive beamformer sums radio frequency data. Other receive beamformers may be used.

The receive beamformer 16 is configured to form receive beams in response to the transmit beams. For example, the receive beamformer 16 receives one, two, or more receive beams in response to each transmit beam for measuring. The phase rotators, delays, and/or summers may be repeated for parallel receive beamformation. One or more of the parallel receive beamformers may share parts of channels, such as sharing initial amplification. The receive beams are collinear, parallel and offset or nonparallel with the corresponding transmit beams.

The receive beamformer 16 is configured to output samples for a single location or multiple locations in a patient. The receive beamformer 16 outputs samples representing locations on-axis with the ARFI beam or within the higher intensity region 46 of the ARFI transmit beam. The samples are on-axis, such as at multiple depths along the ARFI scan line or locations in the high intensity region 46 alongside the ARFI scan line. While the locations are relative to the ARFI transmit beam location, samples from echoes of the ARFI transmit beam are not formed. The samples are from echoes of transmit beams transmitted for measuring tissue displacement.

Once the channel data is beamformed or otherwise combined to represent locations along the scan line 11, the data is converted from the channel domain to the image data domain. By repeating the transmit and receive operations, samples representing the location over time are acquired.

Beamformed samples for measuring tissue displacement caused by the ARFI at the focal region are output.

The image processor 22 is a digital signal processor, a general processor, an application specific integrated circuit (ASIC), field programmable gate array (FPGA), control processor, digital circuitry, analog circuitry, graphics processing unit, combinations thereof, or other now known or later developed device for measuring on-axis displacements from beamformed samples and estimating attenuation and/or or other tissue characteristic from the displacements. The image processor 22 is configured by hardware, firmware, and/or software, such as operating pursuant to instructions provided in the memory 28 or a different memory. In one embodiment, the image processor 22 is a digital signal processor, ASIC, Doppler detector, or FPGA specifically for performing correlation or other displacement calculation, and another device (e.g., calculator or processor) for estimating the attenuation. In other embodiments, the image processor 22 is a programmable device that performs both the displacement calculation and estimation.

The image processor 22 is configured to estimate attenuation at the focal region or along a scan line of the ARFI transmit beam. This estimation is based on displacement of the tissue caused by ARFI, not an induced shear wave. Without tracking a shear wave in the patient, the image processor 22 estimates the attenuation from displacements in the ARFI focal or high intensity region along the ARFI scan line.

The image processor 22 generates displacements from the beamformed samples. Using correlation or other similarity measure, the amount of tissue displacement at different depths is determined from a reference scan of the tissue and scans during tissue movement. The displacements at different depths are determined for each of a plurality of times, providing displacement profiles for the depths.

Using the displacement profiles, the image processor 22 is configured to calculate an attenuation of tissue in the patient. The image processor 22 identifies a peak displacement for each location or depth. Where different displacement profiles are provided for a same depth but separate lateral locations, the displacement profiles may be averaged prior to identifying the peak displacement over time for that depth. Other profile characteristics than peak may be used, such as slope during relaxation.

The image processor 22 is configured to load peak displacements for a phantom acquired using the same ARFI beamformer settings. A ratio or other relative measure of the patient to phantom profile characteristic (e.g., peak displacements) is calculated and converted to linear as a function of depth (e.g., log of the ratio of the peak displacements of the patient tissue to the phantom). The image processor 22 fits a line to the log of the relative measure.

The image processor 22 is configured to calculate the attenuation from the slope of the line. The attenuation known for the phantom or reference and the slope are used to determine the attenuation for the tissue of the patient. The image processor 22 may be configured to calculate an elastic modulus, absorption, scattering, or combinations thereof. The intercept of the line is used to calculate other tissue characteristics. The slope and/or other information may be used, such as estimating elasticity from shear wave velocity measurements, calculating the acoustic absorption from the elasticity and intercept, and calculating the scattering from the absorption and the attenuation.

The samples or other ultrasound data may be used to generate an image. A B-mode detector, flow estimator (e.g., Doppler processor), or other detector may be provided for detecting characteristics from the receive beamformed samples. A B-mode detector detects the intensity or power of the acoustic backscatter. A flow estimator detects the velocity, energy, or variance of moving objects (e.g., tissue or fluid). The detection may be used to generate an image from which a region of interest for attenuation or other tissue characteristic measurement is selected or on which the estimated attenuation or other tissue characteristic is displayed.

The detector, estimator, and/or the image processor 22 are configured to generate an image. The image includes the tissue characteristic. For example, a graph of the attenuation by location or as a function of frequency is generated as an image. As another example, alphanumeric text is generated as an image, such as "attenuation=4.17 dB/cm." In other embodiments, the tissue characteristic value is provided as an annotation on an image of the patient, such as on a B-mode image. In yet other embodiments, one or more pixels corresponding to locations at which the tissue characteristic is estimated are modulated, such as with color, to show the value or values of the viscoelastic parameter.

The memory 28 is video random access memory, random access memory, removable media (e.g. diskette or compact disc), hard drive, database, or other memory device for storing data. The memory 28 is used by the image processor 22 for storing samples, displacements, displacement profile characteristics, relative measurement (e.g., ratio and/or log of the ratio), a fit line, and/or an estimated tissue characteristic. The memory 28 also stores the reference information, such as peak displacements as a function of depth and known tissue characteristics for the reference. Multiple tables or sets of information may be provided, such as a different set for each of a plurality of possible ARFI configurations (e.g., frequency, amplitude, focal locations, apertures, . . . ).

The instructions for implementing the processes, methods and/or techniques discussed above are provided on computer-readable storage media or memories, such as a cache, buffer, RAM, removable media, hard drive or other computer readable storage media, such as represented by the memory 28. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 27 is a CRT, LCD, plasma, projector, monitor, printer, touch screen, or other now known or later developed display device. The display 27 receives RGB, other color values, or other values and outputs an image. The image may be a gray scale or color image. The image displays information that is a function of the tissue characteristic, such as showing attenuation. Alphanumeric, graphical, annotation, or other representation of the tissue characteristic or values derived from the tissue characteristic is displayed in an image on the display 27. The image may or may not additionally represent the region of the patient scanned by the beamformer 12, 16 and transducer 14.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for characterizing tissue with a medical diagnostic ultrasound scanner, the method comprising:
   transmitting from a transducer an acoustic radiation force impulse by the ultrasound scanner as a transmit beam along a scan line in a patient;
   measuring, by the ultrasound scanner, displacements as a function of time along the scan line, at least some of the displacements responsive to the acoustic radiation force impulse;
   determining, by an image processor, a characteristic of the displacements as a function of time for each of a plurality of locations along the scan line;
   calculating, by the image processor, a log of a ratio of the characteristic to a characteristic of a phantom for each of the locations;
   fitting, by the image processor, a line to the log of the ratio as a function of the locations;
   calculating, by the image processor, an attenuation coefficient, absorption coefficient, scattering coefficient, elastic modulus, or combinations thereof using the line; and
   generating on a display an image of the attenuation coefficient, absorption coefficient, scattering coefficient, elastic modulus, or combinations thereof.

2. The method of claim 1 wherein measuring comprises measuring with receive beams collinear with the scan line.

3. The method of claim 1 wherein measuring comprises measuring with simultaneous receive beams along receive lines that are positioned at locations with intensities within 3 dB below a peak intensity within a beam profile of the transmit beam.

4. The method of claim 1 wherein measuring comprises measuring before the transmitting of the acoustic radiation force impulse and a plurality of times after the transmitting of the acoustic radiation force impulse.

5. The method of claim 1 wherein measuring comprises measuring the displacements as tissue relaxes after ceasing of the acoustic radiation force impulse at the locations, the locations including a focal location of the acoustic radiation force impulse.

6. The method of claim 1 wherein measuring comprises generating a time-domain profile of the displacements as a function of the time.

7. The method of claim 1 wherein determining comprises determining a maximum displacement of the displacements for each of the locations.

8. The method of claim 7 wherein calculating the log of the ratio comprises calculating, for each of the locations, the log of the ratio of the maximum displacement to a phantom maximum displacement of the phantom.

9. The method of claim 1 wherein calculating the attenuation coefficient, absorption coefficient, scattering coefficient, elastic modulus, or combinations thereof comprises calculating the attenuation coefficient from a slope of the line.

10. The method of claim 9 wherein calculating the attenuation coefficient, absorption coefficient, scattering coefficient, elastic modulus, or combinations thereof comprises calculating the elastic modulus, the absorption coefficient, or both from an intercept of the line.

11. The method of claim 10 wherein calculating the attenuation coefficient, absorption coefficient, scattering coefficient, elastic modulus, or combinations thereof comprises calculating the scattering coefficient from the attenuation coefficient and the absorption coefficient.

12. The method of claim 1 wherein generating comprises generating the image with a pixel modulation, graph, or alphanumeric text for the attenuation coefficient, absorption coefficient, scattering coefficient, elastic modulus, or combinations thereof.

13. A system for ultrasound imaging, the system comprising: a transmit beamformer configured to transmit an acoustic pushing pulse to a focal region in a patient;
   a receive beamformer configured to output samples for regions on-axis with the pushing pulse;
   an image processor configured to determine displacements for the regions from the samples and to calculate an attenuation of tissue in the patient from the displacements caused by the acoustic pushing pulse without displacements from another acoustic pushing pulse; and
   a display configured to display the attenuation;
   wherein the image processor is configured to generate the displacements as a function of time at the focal region from the samples, to identify peak displacement for each of the regions, to fit a line to a log of a ratio of the peak displacements to peak displacements in a phantom with a measured attenuation, and to calculate the attenuation from a slope of the line.

14. The system of claim 13 wherein the acoustic pushing pulse comprises an acoustic radiation force impulse as a transmit beam focused at the focal region, and wherein the samples are beamformed samples from tracking tissue displacement caused by the acoustic radiation force impulse at the focal region.

15. The system of claim 13 wherein the image processor is configured to calculate an elastic modulus, absorption, scattering, or combinations thereof from an intercept of the line.

16. A method for ultrasound imaging with a medical diagnostic ultrasound scanner, the method comprising:
   tracking, by a beamformer of the ultrasound scanner, displacements along an axis of excitation of a single acoustic radiation force impulse in a tissue of a patient, the displacements caused by the single acoustic radiation force impulse;
   estimating, by an image processor of the ultrasound scanner, an attenuation from the displacements of just the single acoustic radiation force impulse, the displacements being along the axis; and
   displaying the attenuation;
   wherein estimating comprises estimating the attenuation from a slope of a line fit to a log of a ratio of the displacements along the axis to the displacements from the phantom with the known attenuation.

17. The method of claim 16 further comprising estimating an absorption coefficient, a scattering coefficient, or both from an intercept of the line.

* * * * *